(12) United States Patent
Rust et al.

(10) Patent No.: US 10,768,084 B2
(45) Date of Patent: *Sep. 8, 2020

(54) ACCELERATED PAVEMENT TESTING

(71) Applicant: CSIR, Pretoria (ZA)

(72) Inventors: Frederick Christoffel Rust, Pretoria (ZA); Morris De Beer, Pretoria (ZA)

(73) Assignee: CSIR (ZA)

( * ) Notice: Subject to any disclaimer, the term of this patent is extended or adjusted under 35 U.S.C. 154(b) by 0 days.

This patent is subject to a terminal disclaimer.

(21) Appl. No.: 16/662,927

(22) Filed: Oct. 24, 2019

(65) Prior Publication Data
US 2020/0056969 A1 Feb. 20, 2020

Related U.S. Application Data

(62) Division of application No. 15/557,758, filed as application No. PCT/IB2017/050220 on Jan. 16, 2017, now Pat. No. 10,495,556.

(30) Foreign Application Priority Data

Feb. 26, 2016 (ZA) ................................. 2016/01321

(51) Int. Cl.
*G01N 3/36* (2006.01)
*G01N 33/42* (2006.01)
(Continued)

(52) U.S. Cl.
CPC ................. *G01N 3/36* (2013.01); *G01N 3/08* (2013.01); *G01N 3/32* (2013.01); *G01N 33/42* (2013.01);
(Continued)

(58) Field of Classification Search
CPC .. G01N 3/02; G01N 3/08; G01N 3/32; G01N 3/36; G01N 3/42; G01N 33/383;
(Continued)

(56) References Cited

U.S. PATENT DOCUMENTS

| | | | |
|---|---|---|---|
| 5,614,670 | A | 3/1997 | Nazarian et al. |
| 5,641,901 | A | 6/1997 | Powell |

(Continued)

FOREIGN PATENT DOCUMENTS

| | | |
|---|---|---|
| CN | 1032398 | 4/1989 |
| WO | 2013152293 | 10/2013 |

OTHER PUBLICATIONS

Wynand JVDM Steyn; "Significant Findings from Full-Scale Accelerated Pavement Testing": The National Academies Press; Nov. 5, 2012; Washington, D.C., USA.
(Continued)

*Primary Examiner* — Benjamin R Schmitt
(74) *Attorney, Agent, or Firm* — Clark Hill PLC; James R. Foley

(57) ABSTRACT

A method of testing pavement includes repeatedly simulating wheel loading on the pavement by repeatedly applying a plurality of discrete forces with a downwards component, in series and one after the other, to an upper surface of a test strip of the pavement thereby to simulate a load exerted by a travelling wheel and hence subjecting the pavement to accelerated testing. The discrete forces are provided by repeatedly actuating a series of actuators, one after the other, each to exert a force with a downwards component to the upper surface of the test strip of pavement, or to a portion thereof.

11 Claims, 3 Drawing Sheets

Figure 1:
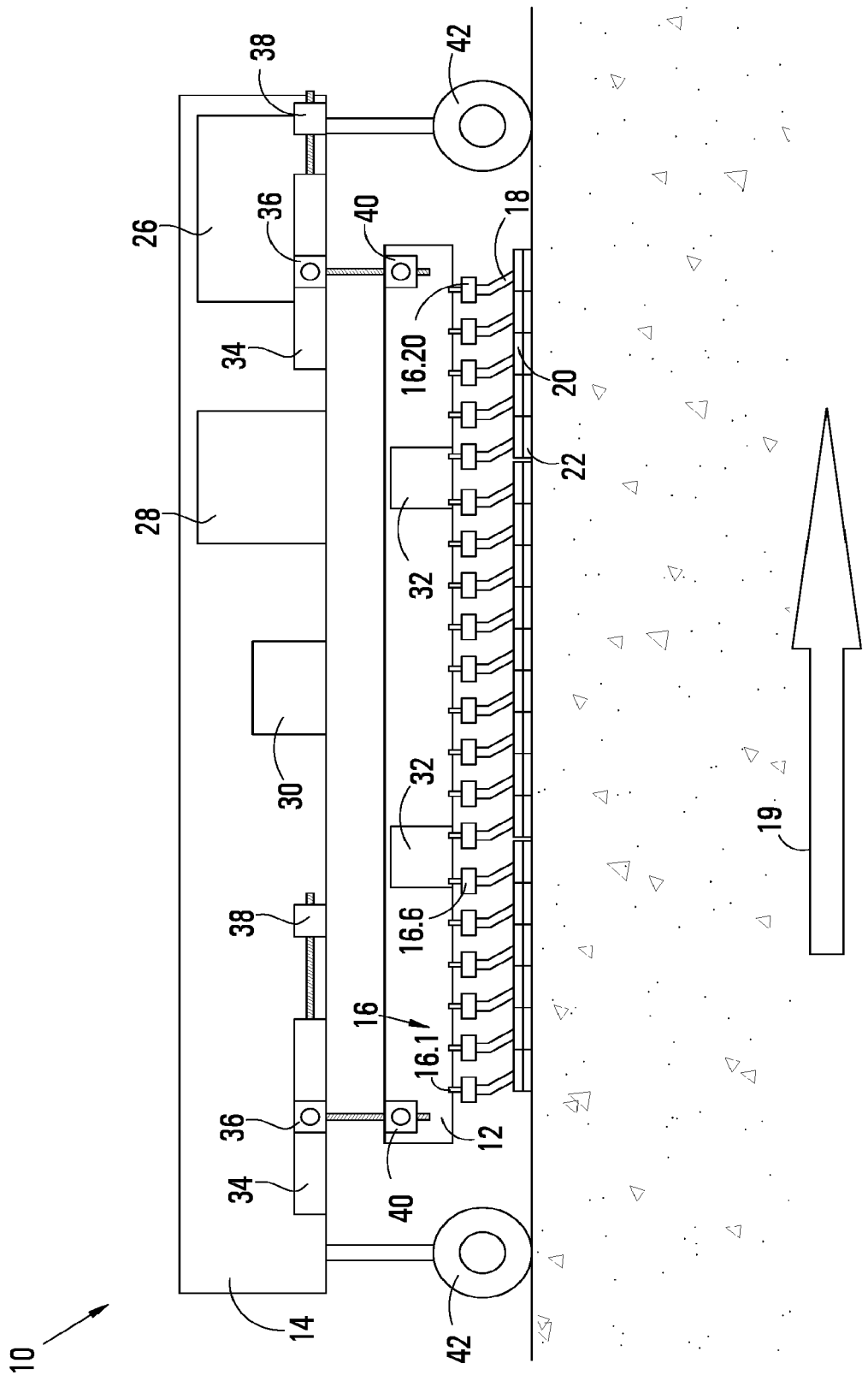

(51) Int. Cl.
*G01N 3/08* (2006.01)
*G01N 3/32* (2006.01)
*E01C 19/34* (2006.01)

(52) U.S. Cl.
CPC ...... *E01C 19/34* (2013.01); *G01N 2203/0048* (2013.01)

(58) Field of Classification Search
CPC ........... G01N 33/42; G01N 2203/0042; G01N 2203/0048; E01C 19/30; E01C 19/34
USPC .................. 73/786, 788, 794, 865.6, 866
See application file for complete search history.

(56) References Cited

U.S. PATENT DOCUMENTS

| | | |
|---|---|---|
| 5,659,140 A | 8/1997 | Jakob et al. |
| 2007/0235250 A1 | 10/2007 | Krumhansl et al. |
| 2012/0103106 A1 | 5/2012 | Feng et al. |

OTHER PUBLICATIONS

Federal Highway Research Institute (BASt); "Dynamic Full Scale Pavement Test Facilities"; Jul. 2009; Germany.

ACCELERATED PAVEMENT TESTING

THIS INVENTION relates to accelerated pavement testing. In particular, the invention relates to a method of testing pavement, and to an accelerated pavement testing device, also known as a heavy vehicle simulator.

Transport infrastructure is a major enabler for socio-economic development and growth. Road pavements are expensive and constitute a valuable asset to any country. In South Africa alone the replacement value of the road infrastructure is in excess of R2 trillion (about US$ 0.13 trillion), an investment that needs to be protected and sustained. Although current pavement design methods are advanced, there is continuous development of new materials, design and construction technologies that need to be evaluated thoroughly before they are mainstreamed into industry. This is of particular importance in view of the fact that a 4 lane highway can cost up to R50 million (about US$ 3.13 million) per km to design and construct in South Africa.

Under normal circumstances a road pavement is designed to last between 20 and 30 years. Therefore if a new material or method is introduced one needs to construct a test section and subject it to 10 to 20 years of traffic before the concept is considered as proven. This is a very time consuming exercise with significant opportunity cost associated with it. The alternative is to subject the test section to accelerated pavement testing (APT), which can provide an indication of the potential performance of the section in a few months. Ideally one needs to evaluate a test section on a real constructed road rather than in a laboratory situation to ensure real subgrade conditions, real construction processes, etc. This implies that the testing device must be mobile and transportable to the test site, preferably on a real road. The three main mobile APT devices that currently exist include the South African Heavy Vehicle Simulator (HVS), the Australian Accelerated Load Facility (ALF) and the Mobile Load Simulator (MLS). All these devices are based on a single or on multiple dual tyre truck bogie(s) that run repetitively on a pavement test section to simulate heavy traffic. However, they all have a number of disadvantages. These include:

The speed of testing is low, less than 25 km/h, due to the physical configuration of the device and the energy required to accelerate the bogie to testing speed as well as the problem of containing the resultant forces on the test frame caused by a test bogie of several tons being accelerated, decelerated or cornered (in the case of a circular MLS);

The loading produced by the apparatus can be low due to the slowness of the moving wheel load as well as the configuration, which implies a lengthy test period to simulate the equivalent of 10 or 20 years of traffic loading;

The continuous stream of traffic simulated by these devices (especially the MLS) could cause the pavement to remain in a stressed state during testing that does not accurately reflect real conditions due to the fact that there are no rest periods between loading. Almost all pavement materials display some elastic recovery after loading and thus this continuously stressed state does not reflect accurately the stressed state in real pavements;

Real traffic causes dynamic loading on a road pavement due to the movement of a vehicle body on its suspension as well as due to so-called tyre hop caused by irregularities in the road surface. None of these devices can accurately simulate these dynamics. In addition, both the ALF and the MLS wheel bogies come onto the pavement from a height at speed that causes dynamic loading that is not experienced from normal traffic loading on pavements.

A real traffic stream consists of a mix of axle types, speeds, single or grouped axles (up to 4 in a group) and various axle loads. None of the existing devices can simulate this accurately.

There thus exists a need for a method of testing pavement and an accelerated pavement testing device that do not suffer from at least some of the aforementioned disadvantages.

According to one aspect of the invention, there is provided a method of testing pavement, the method including repeatedly simulating wheel loading on the pavement by repeatedly applying a plurality of discreet forces with a downwards component, in series and one after the other, to an upper surface of a test strip of the pavement thereby to simulate a load exerted by a travelling wheel and hence subjecting the pavement to accelerated testing.

The response and degradation of the test strip of pavement over time can advantageously be used to understand and model pavement behaviour, improve design methods, test the performance of pavement materials and predict the future performance of pavements.

Typically, the series of discreet forces is a linear series or array. Thus, the test strip of pavement being subjected to the series of discrete forces is typically a linear strip of pavement.

The discreet forces may be provided by repeatedly actuating a series of actuators, one after the other, each to exert a force with a downwards component to the upper surface of the test strip of pavement, or to a portion thereof.

The actuators may be actuated electrically, hydraulically or pneumatically, preferably electrically or hydraulically.

The discreet forces may each be exerted by a rectangular in outline force transfer element or sole. Such a sole thus simulates a vehicle tyre footprint. Each sole is typically carried at or connected to a free, displaceable end of an associated actuator, or of a member driven by an associated actuator. More than one sole may be carried by or connected to an actuator.

The sole may have a length between about 150 mm and about 400 mm, preferably between about 250 mm and about 350 mm, more preferably between about 290 mm and about 310 mm, e.g. about 300 mm.

The sole may have a width of between about 100 mm and about 300 mm, preferably between about 150 mm and about 250 mm, more preferably between about 190 mm and about 210 mm, e.g. about 200 mm.

The sole may be of rubber, whether natural rubber or synthetic rubber.

The sole may have a tyre tread pattern on a bottom surface thereof.

In one embodiment of the invention, the sole is a treaded portion of a commercially available tyre, typically a treaded rectangular portion of a heavy vehicle tyre.

The sole may have a substantially uniform thickness, disregarding thickness variations caused by recesses or grooves of a tread pattern. The thickness of the sole may be between about 15 mm and about 50 mm, preferably between about 15 mm and about 25 mm, more preferably between about 20 mm and about 25 mm, e.g. about 22 mm.

The sole may be fitted to an associated shoe carried by or connected to an associated actuator. Typically, the shoe is of metal, e.g. steel. More than one shoe may be carried by or connected to an actuator.

In one embodiment of the invention, the shoe has a planar or flat bottom surface. Such a shoe advantageously can be used to test the effect of a uniform wheel or tyre loading on pavement.

In another embodiment of the invention, the shoe has a concave bottom surface, i.e. a parabolic bottom surface with an elongate concavity or depression being arranged centrally along a longitudinal axis of the shoe, i.e. along the direction of the strip of pavement being tested. Such a shoe advantageously can be used to test the effect of an under-inflated tyre on pavement.

In a further embodiment of the invention, the shoe has an inverse parabolic bottom surface, i.e. a convex bottom surface with an elongate downwardly projecting bulge being arranged centrally along a longitudinal axis of the shoe, i.e. along the direction of the strip of pavement being tested. Such a shoe advantageously can be used to test the effect of an over-inflated tyre on pavement.

As will be appreciated, the method of the invention may include using a plurality of different-shaped shoes during a single test run. Thus, different longitudinally positioned portions of the strip of pavement being tested may be subjected to discreet forces with a downwards component, where the forces applied to one portion of the test strip of pavement are transferred by soles each carried by an associated particularly shaped shoe, and the forces applied to a different portion of the test strip of pavement are transferred by soles each carried by an associated shoe of another, different shape.

The discreet forces may be vertical forces.

The discreet forces may be transferred from an actuator to its associated shoe(s) or sole(s) by means of a force transfer member. At least a portion of the force transfer member may be at an angle to the vertical or at an angle to an axis of movement of its associated actuator. In other words, a sole may be displaced relative to the axis of movement of its associated actuator. The sole may in particular be forwardly displaced relative to the axis of movement of its associated actuator. The axis of movement of the actuator in one embodiment of the invention thus does not coincide with a centre of its associated shoe or sole.

Said angle to the vertical or said angle to the axis of movement of the associated actuator of the force transfer member may be between about 1° and about 30% preferably between about 8° and about 25°, more preferably between about 12° and about 20°, e.g. about 15°.

Typically, the angle to the vertical or the angle to the axis of movement of the associated actuator of the force transfer member is away from the direction of wheel travel being simulated.

Advantageously, with discreet forces being transferred between an actuator and its associated shoe(s) or sole(s) by means of a force transfer member that is at an angle to the vertical, the effect of both vertical and horizontal force components exerted on pavement by a travelling wheel can be determined under accelerated test conditions.

Preferably, at least 5, more preferably at least 15, even more preferably at least 20, most preferably at least 30 discreet forces with a downwards component are repeatedly applied to the test strip of pavement, as a series of forces. It is however to be appreciated that not all of the discrete forces are necessarily required to simulate a single wheel or a single pair of wheels; a selected group of forces may be used to simulate a wheel or a pair of wheels travelling over a portion of the strip(s) of pavement which is shorter than the entire strip(s) of pavement being subjected to discrete forces.

Each test strip of pavement may have a length of between about 3 m and about 12 m, preferably between about 5 m and about 10 m, more preferably between about 6 m and about 10 m, e.g. about 10 m.

If desired, two or more, e.g. two, series each of a plurality of discreet forces with a downwards component may be applied to the upper surface of strips of pavement as hereinbefore described, with the two or more series being adjacent one another and being applied parallel to one another. In other words, two parallel typically linear strips of pavement may simultaneously be subjected to accelerated testing. In one embodiment of the invention, this is achieved by transferring force from each actuator to two adjacent, laterally spaced associated shoes. The adjacent, laterally spaced shoes may be attached to a single, common force transfer member. In this way, wheel loading exerted by dual treaded tyres can for example be simulated. Using different soles and/or different shoes for each test strip of pavement, the effect of wheel loading exerted by different types of tyres and/or differently inflated tyres can be investigated on two parallel test strips of pavement.

Typically, in order to simulate a single wheel load on a test strip of pavement or a portion thereof, the series of discreet forces are applied in a fixed sequence, starting at one end of the strip of pavement or portion thereof upstream of a direction of wheel travel being simulated and ending at another end of the strip of pavement or portion thereof, and being repeated over and over again for a test period.

A downwards component of each discreet force in a series of discreet forces may have a magnitude of between about 5 kN and about 100 kN, preferably between about 15 kN and about 80 kN, more preferably between about 20 kN and about 60 kN, e.g. about 40 kN.

The discreet forces in a series may each be applied at a frequency of between about 0.5 Hz and about 30 Hz, preferably between about 1 Hz and about 28 Hz, e.g. about 27 Hz.

The application of the discreet forces may be controlled by a processor. The processor may be programmable.

The processor may be programmable to adjust the magnitudes of the discreet forces applied to the upper surface of the pavement. In this way, the method of the invention can simulate and test the effect of different wheel loads.

The processor may be programmable to adjust the frequency at which the discreet forces are applied to the upper surface of the pavement. In this way, the method of the invention can simulate and test the effect of different wheel speeds, e.g. up to 50 km/h.

The processor may be programmable to adjust the magnitude of the discreet forces applied to the upper surface of the pavement, at one or more positions in the series of forces, compared to other positions in the series of forces, so that the force(s) applied at said one or more positions differs from the force(s) applied at other positions in the series. In this way, the method of the invention can simulate and test the effect of dynamic loading on the pavement.

The processor may be programmable to adjust the magnitude of the discreet forces applied to the upper surface of the pavement during a test period compared to the magnitude of the discreet forces applied to the upper surface of the pavement during another test period. In this way, the method of the invention can simulate and test the effect of dynamic loading on the pavement.

The processor may be programmable to vary the sequence in which the discreet forces are applied to the upper surface of the pavement. In this way, the method of the invention can simulate and test the effect of wheels carried on multiple axles on the pavement. The method can also vary the axle distance between simulated heave vehicle axles (i.e. the distance between a footprint of a leading wheel and a footprint of a following wheel), and/or the lead time between heavy vehicles.

The processor may be programmable to adjust a period between the application of said discreet forces simulating wheel loading, whether wheel loading from a single axis or from or multiple axis is simulated. In this way, the method of the invention can simulate and test the effect of rest periods between wheel travel on the pavement.

If a tyre load is applied to a road surface it will cause both an elastic deformation as well as a plastic deformation. Repeated tyre loads in exactly the same place will cause edge effects that will lead to unnatural deformation of the road surface. The method of the invention may thus include displacing the series of applied discreet forces from time to time so that a target impact area of each of the discreet forces changes. The series of applied discreet forces may be displaced forwards or backwards, parallel to the series of applied discreet forces. Instead, or in addition, the series of applied discreet forces may be displaced sideways to the left or to the right of the series of applied discreet forces. The method of the invention may thus include simulating the effect of wandering tyres on pavement, avoiding unnatural plastic deformation through edge effects at a simulated tyre/pavement interface.

Displacing the series of applied discreet forces may include interrupting the application of the series of discreet forces, lifting all of the soles clear of the upper surface of the pavement, displacing the actuators to a new location, and commencing application of the plurality of discreet forces to the upper surface of a new strip of the pavement. Typically, the new strip of pavement overlaps with a previous strip of pavement subjected to testing.

The method of the invention may include measuring deformation of the upper surface of the pavement. Both elastic and plastic deformation of the upper surface may be measured, e.g. by means of laser detection. Measuring methods and devices for doing so are known to those skilled in the art.

Measurement of the deformation of the upper surface of the pavement may be made through a gap between two adjacent soles, and may thus take place during a test run without the need to stop the test run. Measurement of surface deflection may also be made through a gap between two adjacent soles, and may thus take place during a test run without the need to stop the test run or alternatively can be made through a hole in the sole.

According to another aspect of the invention, there is provided an accelerated pavement testing device which includes
a carrier; and
an array of actuators carried by the carrier and configured each rapidly and repeatedly to apply a discrete force with a downwards component to an upper surface of a test strip of pavement, each actuator being associated with at least one force transfer element or sole configured in use to transfer said discreet force from the actuator to pavement being tested thereby to simulate a load exerted by a travelling wheel to said test strip of pavement and hence to subject the pavement to accelerated testing.

The array of actuators may be a linear array of actuators and may be configured rapidly and repeatedly to apply at least some of said discreet forces in series and one after the other.

The actuators may be as hereinbefore described.

The force transfer element may be as hereinbefore described.

A spacing between a majority of adjacent force transfer elements or soles arranged in a one-dimensional array, e.g. a linear array, may be between about 1 mm and about 10 mm, preferably between about 3 mm and about 7 mm, more preferably between about 4 mm and about 6 mm, e.g. about 5 mm. It is however to be appreciated that a spacing between at least one pair of adjacent force transfer elements or soles may be larger, e.g. to allow a space for measurement apparatus to operate.

Each actuator may carry one or more shoes as hereinbefore described. The device may thus be configured to test two parallel adjacent strips of pavement, typically simultaneously, as hereinbefore described.

The actuators may be arranged, when the carrier is horizontal, to apply vertically downward forces.

The device may include a force transfer member between an actuator and its associated force transfer element. The force transfer member may be elongate and/or may be at an angle to the axis of movement of its associated actuator as hereinbefore described.

Preferably, the device includes at least 5, more preferably at least 15, even more preferably at least 20, most preferably at least 30 actuators. Preferably, all of these actuators are arranged in a single one-dimensional array or linear array.

Each actuator may be configured to apply a discreet force with a downwards component with a magnitude as hereinbefore described.

Each actuator may be configured to apply a discreet force with a downwards component at a frequency as hereinbefore described.

In one embodiment, each actuator is configured to apply a discrete force with a downwards component that has a magnitude of between 5 kN and 100 kN and at a frequency of between 0.5 Hz and 30 Hz.

The device may include a frame or chassis supporting or carrying the carrier. In one embodiment of the invention, the carrier is suspended below the frame or chassis.

The frame or chassis, together with other components of the accelerated pavement testing device, is typically sufficiently heavy to counteract the forces applied by the actuators in use so that the device does not bounce or hop as a result of application of the discreet forces applied by the actuators. If desired or necessary, the frame or chassis may carry one or more weights to increase the weight of the device.

The frame or chassis may be wheeled, rendering the device mobile.

The carrier may be vertically adjustable relative to the frame or chassis. The device may thus include one or more linear actuators to displace the carrier vertically relative to the frame or chassis. In one embodiment of the invention, a plurality of worm gear linear actuators, e.g. electrically driven worm gear linear actuators, is provided for purposes of lifting and lowering the carrier relative to the frame or chassis.

The carrier may be adjustable in a plane parallel to a plane in which the frame or chassis is positioned. Thus, if the frame or chassis is positioned in a first horizontal plane, the carrier may be adjustable in a second horizontal plane relative to the frame or chassis. The carrier may be adjustable in a lateral direction, i.e. to the left or to the right. Instead, or in addition, the carrier may be adjustable in a longitudinal direction, i.e. forwards or backwards. The device may thus include one or more linear actuators to displace the carrier in a plane parallel to a plane in which the frame or chassis is positioned. In one embodiment of the invention, a plurality of worm gear linear actuators, e.g. electrically driven worm gear linear actuators, is provided for purposes of displacing the carrier in a plane parallel to the plane of the frame or chassis.

The device may include a generator for generating electricity. The device may also include a fuel tank for the generator. Typically, the generator and/or fuel tank is/are supported on or by the chassis or frame.

The device may include a hydraulic power plant, e.g. a hydraulic fluid reservoir and a hydraulic pump and associated hydraulic control equipment and lines. Typically, the hydraulic power plant, when present, is supported on or by the chassis or frame and is used to power hydraulic actuators.

The device may include a processor as hereinbefore described. The processor may be supported on or by the chassis or frame.

In one embodiment of the invention, the device thus includes a programmable controller to control the application of the discreet forces by the actuators, the processor being programmable to adjust one or more of:

the magnitudes of the discreet forces applied to the upper surface of the pavement to simulate and test the effect of different wheel loads;

the frequency at which the discreet forces are applied to the upper surface of the pavement to simulate and test the effect of different wheel speeds;

the magnitude of the discreet forces applied to the upper surface of the pavement by one or more actuators compared to other actuators, so that the force(s) applied by said one or more actuators differs from the force(s) applied by other actuators to simulate and test the effect of dynamic loading on the pavement;

the magnitude of the discreet forces applied to the upper surface of the pavement during a test period compared to the magnitude of the discreet forces applied to the upper surface of the pavement during another test period to simulate and test the effect of dynamic loading on the pavement;

the sequence in which the discreet forces are applied to the upper surface of the pavement to simulate and test the effect of wheels carried on multiple axles on the pavement; and a period between the application of said discreet forces simulating wheel loading, whether wheel loading from a single axis or from or multiple axis is simulated, to simulate and test the effect of rest periods between wheel travel on the pavement.

The device may include measurement equipment, e.g. laser measurement equipment, to measure deformation and/or deflection of an upper surface of pavement. The measurement equipment may be configured to measure the deformation of the upper surface of the pavement through a gap between two adjacent soles or through a hole in the sole, whilst the device is in use. Thus, in one embodiment of the invention, a gap between at least one pair of adjacent soles in a linear array of soles is at least 5 mm, preferably at least 10 mm, more preferably at least 15 mm, e.g. 15 mm or 20 mm.

Figure 2:
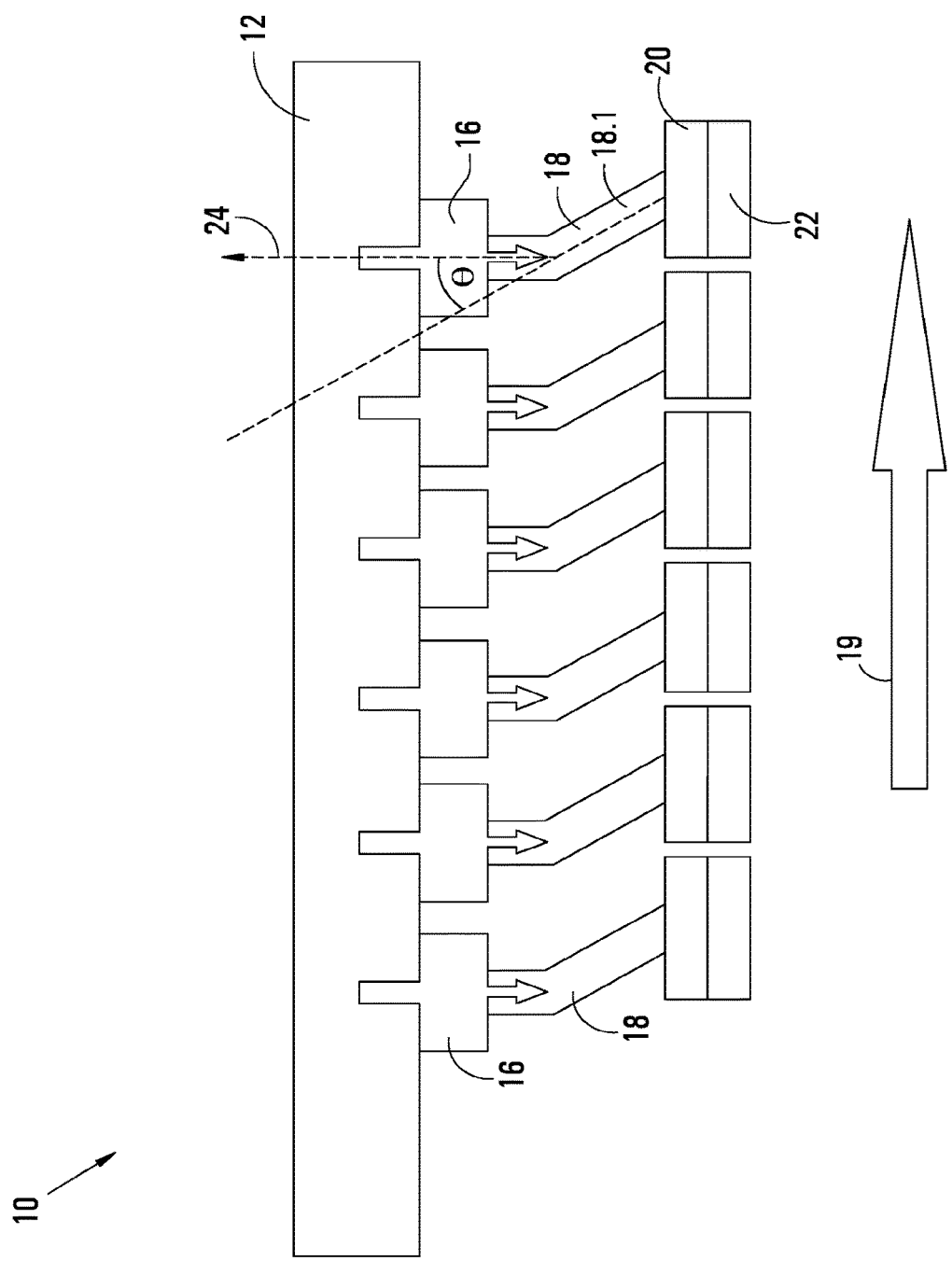
Figure 3:
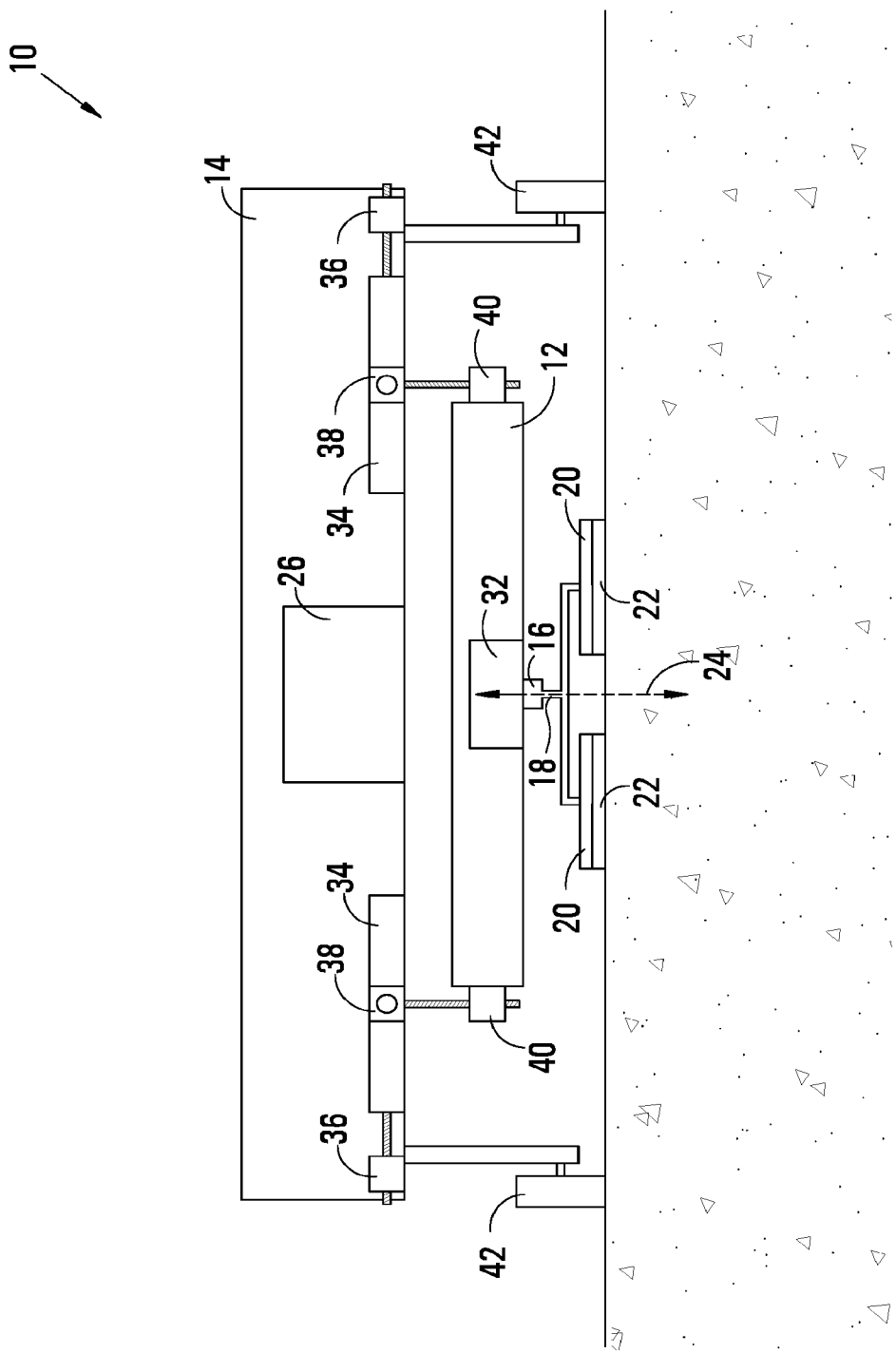

The invention will now be described, by way of example, with reference to the accompanying diagrammatic drawings, in which FIG. 1 shows a side view of an accelerated pavement testing device in accordance with the invention;

FIG. 2 shows an enlarged side view of a portion of the accelerated pavement testing device of FIG. 1; and FIG. 3 shows a front view of the accelerated pavement testing device of FIG. 1.

Referring to the drawings, reference numeral 10 generally indicates an accelerated pavement testing device in accordance with the invention. The device 10 includes a heavy steel carrier 12 suspended below a heavy steel wheeled frame or chassis 14 and a linear array of twenty hydraulic actuators 16 mounted to the carrier 12, along a centre line of the carrier 12 (see FIG. 3).

Each hydraulic actuator 16 acts on an elongate force transfer member 18 ending in a pair of steel shoes 20 with a rectangular footprint. A force transfer element or sole 22, also with a rectangular footprint, is attached to each steel shoe 20, as can be better seen in FIG. 2 and FIG. 3.

The hydraulic actuators 16 are arranged to act perpendicularly to a plane in which the carrier 12 is located. Thus, when the carrier 12 is in a horizontal plane, the actuators 16 are arranged to act vertically to supply a vertically downwardly directed discreet force via the force transfer member 18, steel shoes 20 and soles 22 to a pair of rectangular areas of pavement each forming part of an associated elongate strip of pavement undergoing accelerated testing.

As indicated hereinbefore, each steel shoe 20 is rectangular in outline, i.e. in plan, and has a length of about 300 mm and a width of about 200 mm. Similarly, each sole has a length of about 300 mm and a width of about 200 mm. In the embodiment shown in the drawings, the steel shoes 20 all have planar bottom surfaces. As will be appreciated, the bottom surfaces of the steel shoes may be configured differently, e.g. as a slightly parabolic bottom surface with an elongate concavity or depression arranged centrally along a longitudinal axis of the shoe to test the effect of an under-inflated tyre on pavement, or as an inverse slightly parabolic bottom surface, i.e. a slightly convex bottom surface with a small elongate downwardly projecting bulge being arranged centrally along a longitudinal axis of the shoe to test the effect of an over-inflated tyre on pavement.

Each sole 22 is in fact a rectangular treaded portion of a commercially available heavy vehicle tyre that has been adhesively attached to its associated steel shoe 20.

As can clearly be seen in FIG. 3 of the drawings, each actuator 16 thus simultaneously transfers force to a pair of steel shoes 20 with their associated soles 22. As can be more clearly seen in FIG. 2 of the drawings, each force transfer member 18 has a slanted portion 18.1 which is at an angle to a typically vertical axis of movement 24 of its associated actuator 16. In the embodiment of the device 10 of the invention illustrated in the drawings, an angle θ between the slanted portion 18.1 of the force transfer member 18 and the axis of movement 24 of its associated hydraulic actuator 16 is about 15°. The slanted portion 18.1 of the force transfer member 18 leans backwardly away from a direction 19 of wheel travel being simulated by the device 10, as is described in more detail hereinafter.

The accelerated pavement testing device 10 further includes a diesel-powered electric generator 26 supported on or by the frame or chassis 14, a hydraulic power plant 28 and a controller 30 which includes a programmable processor. The hydraulic power plant 28 and the controller 30 are also supported on or by the frame or chassis 14.

The generator 26, hydraulic power plant 28 and controller 30 are only shown schematically without any detail, such as a battery, a diesel fuel tank, fuel lines, a hydraulic fluid reservoir, a hydraulic pump, associated hydraulic control equipment and lines, and the like, which would typically form part of these components.

The accelerated pavement testing device 10 also includes a pair of laser measurement devices 32 supported on the carrier 12. The laser measurement devices 32 are configured to measure deformation of an upper surface of pavement through a gap between two adjacent steel shoes 20 and their associated soles 22. This gap is about 15 mm.

The carrier 12 is adjustable in a plane parallel to a plane in which the frame or chassis 14 is positioned, i.e. typically in a horizontal plane. The frame of chassis 14 is suspended from four slideably displaceable heavy mounts 34, each displaceable mount 34 more or less being located above a corner of the frame or chassis 14. Each mount 34 is connected to a worm gear linear actuator 36 (see FIG. 3) by means of which the mounts 34 can be moved to the left or to the right, thereby moving the carrier 12 to the left or to the right relative to the frame or chassis 14. Similarly, each mount 34 is attached to a worm gear linear actuator 38 (see FIG. 1) connected to the frame or chassis 14. By means of the worm gear linear actuators 38, the mounts 34 can be moved backwards and forwards, thereby moving the carrier 12 backwards or forwards relative to the frame or chassis 14.

The carrier 12 is also adjustable vertically relative to the frame or chassis 14. The carrier 12 is thus suspended from the mounts 34 by means of worm gear linear actuators 40 which allow lifting and lowering of the carrier 12 relative to the frame or chassis 14.

As will be appreciated, in view thereof that significant force and vibrations are generated by the hydraulic actuators 14 and transferred to parallel strips of pavement being tested, the worm gear linear actuators 36, 38 and 40 are sturdy, as are the mounts 34.

The frame or chassis 14 is supported on four wheels 42.

In use, the accelerated pavement testing device 10 is towed to a section of pavement that is to be subjected to accelerated testing. The controller 30 is used to select a test programme in order to simulate specific heavy vehicle traffic over the test section of pavement and the actuators 16 are then used repeatedly to apply a plurality of discreet forces with a downwards component, in series, and at least some of which are one after the other, to an upper surface of two parallel strips of test surfaces of pavement thereby to simulate a load exerted by travelling wheels, as programmed. In this way, the pavement is subjected to accelerated testing.

As will be appreciated, as each actuator 16 is individually controllable by means of the controller 30 and its programmable processor, a very wide variety of streams of flowing traffic can be simulated by the device 10. Only a few of these are described hereinafter.

A first traffic stream that can be simulated by the device 10 is a pair of dual, treaded, heavy vehicle tyres mounted to a common end of a single axle. For this traffic stream, the actuators 14 are controlled to apply discreet downward forces in series and all one after the other, starting from a left-hand actuator 16.1 as shown in FIG. 1 of the drawings and ending with a right-hand actuator 16.20 as shown in FIG. 1 of the drawings. Each actuator 16 applies force at a frequency of about 27 Hz with a magnitude of about 40 kN. At this frequency, a vehicle speed of about 50 km/h is being simulated.

Starting with the left-hand most actuator 16.1, the actuators 16 are thus actuated one after the other in series and all of the actuators 16 are actuated to exert a discreet downwards force, ending with the actuator 16.20, before the left-hand most actuator 16.1 is actuated again, repeating the series over and over. Two parallel test strips of pavement are thus subjected to a loading which simulates the loading exerted by a pair of heavy vehicle tyres travelling in the direction of arrow 19 in FIG. 1. From time to time, when required or as programmed, the laser measurement devices 32 measure elastic and plastic deformation of the upper surface of the test strips of pavement, preferably without interrupting the actuation of the actuators 16, although this may be difficult in view of the vibrating environment within which the laser measurement devices 32 would then have to operate.

If it is required to simulate the effect of wandering tyres on pavement, thereby avoiding unnatural plastic deformation through edge effects at a simulated tyre/pavement interface, the application of the series of discreet forces by means of the actuators 16 may be interrupted, whereafter all of the actuators are actuated to lift the soles 22 free of the upper surface of the test strips of pavement. The carrier 12 is then displaced by means of the worm gear linear actuators 36, if the carrier 12 is to be displaced towards the left or towards the right, or by means of the worm gear linear actuators 38 if the carrier 12 is to be displaced forwards or backwards. Thereafter, testing is continued by applying rapid discreet forces by means of the actuators 16 to the upper surface of the pavement.

In another, cheaper version of the accelerated testing device of the invention (not shown), the wheels 42 are used to displace the entire device, and hence the points of application of the forces exerted by the actuators, forwards or backwards and/or to the left or to the right. This cheaper version of the device thus does not include means to displace the carrier 12 in a plane parallel to the plane of the frame or chassis 14. Instead, the cheaper version may include means to displace the carrier 12 only to the left and to the right, i.e. laterally, in a plane parallel to the plane of the frame or chassis 14. As moving the entire device 10 may be laborious and as it may not be practical to do so frequently enough to simulate the effect of wandering tyres on pavement adequately, the preferred embodiment of the device 10 do include means to displace the carrier 12 in a plane parallel to the plane of the frame or chassis 14, forwards and backwards as well as laterally to the left and to the right.

If it is desired to simulate and test the effect of different wheel loads on the test strips of pavement, the controller 30 can adjust the magnitude of the discreet forces applied by means of the actuators 16 to the upper surface of the pavement.

If it is desired to simulate and test the effect of different wheel speeds on the pavement, the controller 30 can adjust the frequency at which the actuators 16 are actuated, thereby adjusting the frequency at which the discreet forces are applied to the test strips of pavement.

If it is desired to simulate and test the effect of dynamic loading on the pavement, such as is caused by vehicle suspensions and tyre hop, the controller 30 can adjust the magnitude of the discreet forces applied by only some of the actuators 16. In this way, the force applied to the two parallel test strips of pavement will differ in some locations from the force applied at other locations along the lengths of the test strips.

If it is desired to simulate and test the effect of rest periods between wheel travel on the test strips of pavement, the controller 30 can insert a rest period before each series of application of downward forces by the actuators 16, or for example after the series of discreet forces have been applied a pre-selected number of times.

A second traffic stream that can be simulated by the device 10 is a dual axle heavy vehicle with two tyres next to each other at one end of each axle. This requires the selection of a different programme on the controller 30.

In order to simulate travel of four wheels grouped together in two groups of adjacent wheels, it will be necessary to determine the distance between the footprint of a leading simulated wheel and the footprint of a following simulated wheel. Typically, this distance will equate more or less to the combined length of a specific number of soles 22. For example, four soles 22 of 300 mm length each equals more or less to a 1.2 m spacing between leading and following tyre footprints. Thus, to simulate the wheel loading exerted on two parallel test strips of pavement by a dual axle heavy vehicle with dual tyres at one end of each axle, the actuators 16 can be used to apply two series of discreet forces with a downwards component. For example, the left-hand most actuator 16.1 and a sixth actuator 16.6 can be actuated together, each starting a series of forces running from left to right in FIG. 1. Thus, after the actuators 16.1 and 16.6 have been actuated together, the second and seventh actuators are actuated together, followed by the third and eighth actuators, etc. until each series, running from left to right in FIG. 1, has been completed with the actuation of the actuator 16.20 for that series. Naturally, the simulation of the leading wheel will be completed before the simulation of the following wheel, and only the strips of pavement under the last fourteen actuators will represent the effects of wheel loading exerted by both the leading wheel and the following wheel in this example (it would also be possible, with a different programmed activation of the activators 16, to simulate a leading wheel and a following wheel over the entire length of each test strip of pavement). Thereafter, the two series of applied forces are started simultaneously again with the first and sixth actuators 16.1 and 16.6.

Advantageously, the accelerated pavement testing device 10 of the invention, as illustrated, can be used to simulate and test wheel loading exerted by a wide variety of axle types, at axle speeds of up to 50 km/h, with tyre loading of up to 80 kN. The device and method of the invention, as illustrated, can simulate pavement rest periods and dynamic loading, for example caused by tyre hop and vehicle suspensions, as well as the effects of over-inflated and under-inflated tyres.

The invention claimed is:

1. An accelerated pavement testing device which comprises
   a carrier; and
   an array of at least five actuators carried by the carrier, wherein each actuator is configured to repeatedly apply a discrete force with a downwards component to an upper surface of a test strip of pavement, each actuator being associated with at least one force transfer element or sole configured in use to transfer said discrete force from the actuator to pavement being tested, and the actuators in the array being configured repeatedly to be actuated one actuator after the other actuator in series thereby to simulate a load exerted by a travelling wheel to said test strip of pavement and hence over time to subject the pavement to accelerated testing.

2. The accelerated pavement testing device of claim 1, in which the array of actuators is a linear array of at least fifteen actuators.

3. The accelerated pavement testing device of claim 1, in which the actuators are arranged, when the carrier is horizontal, to apply vertically downward forces.

4. The accelerated pavement testing device of claim 1, which comprises a force transfer member between an actuator and its associated force transfer element or sole, the force transfer member being configured to transfer force from the actuator to its associated at least one force transfer element, and the force transfer member being at an angle to an axis of movement of its associated actuator.

5. The accelerated pavement testing device of claim 1, which comprises a frame or chassis supporting or carrying the carrier, the carrier being vertically adjustable relative to the frame or chassis.

6. The accelerated pavement testing device of claim 1, which comprises a programmable controller to control the application of the discreet forces by the actuators, the processor being programmable to adjust one or more of:
   the magnitudes of the discrete forces applied to the upper surface of the pavement to simulate and test the effect of different wheel loads;
   the frequency at which the discrete forces are applied to the upper surface of the pavement to simulate and test the effect of different wheel speeds;
   the magnitude of the discrete forces applied to the upper surface of the pavement by one or more actuators compared to other actuators, so that the force(s) applied by said one or more actuators differs from the force(s) applied by other actuators to simulate and test the effect of dynamic loading on the pavement;
   the magnitude of the discreet forces applied to the upper surface of the pavement during a test period compared to the magnitude of the discrete forces applied to the upper surface of the pavement during another test period to simulate and test the effect of dynamic loading on the pavement;
   the sequence in which the discrete forces are applied to the upper surface of the pavement to simulate and test the effect of wheels carried on multiple axles on the pavement;
   and a period between the application of said discrete forces simulating wheel loading, whether wheel loading from a single axis or from or multiple axis is simulated, to simulate and test the effect of rest periods between wheel travel on the pavement.

7. The accelerated pavement testing device of claim 1, in which each actuator is configured to apply a discrete force with a downwards component that has a magnitude of between 5 kN and 100 kN and at a frequency of between 0.5 Hz and 30 Hz.

8. The accelerated pavement testing device of claim 1, which comprises a frame or chassis supporting or carrying the carrier, the carrier being adjustable in a plane parallel to a plane in which the frame or chassis is positioned.

9. The accelerated pavement testing device of claim 1, in which a spacing between a majority of adjacent force transfer elements or soles in the array of actuators is between 1 mm and 10 mm.

10. The accelerated pavement testing device of claim 1, in which the force transfer elements or soles are rectangular in outline to simulate a vehicle tyre footprint.

11. The accelerated pavement testing device of claim 10, in which the force transfer elements or soles have a length between 150 mm and 400 mm and/or a width between 100 mm and 300 mm.

* * * * *